(12) United States Patent
Wall

(10) Patent No.: US 7,036,501 B2
(45) Date of Patent: May 2, 2006

(54) ORO-PHARYNGEAL AIRWAY WITH BREATH MONITOR

(76) Inventor: W. Henry Wall, 1758 Colt Dr., Dunwoody, GA (US) 30341

(*) Notice: Subject to any disclaimer, the term of this patent is extended or adjusted under 35 U.S.C. 154(b) by 57 days.

(21) Appl. No.: 10/717,890

(22) Filed: Nov. 20, 2003

(65) Prior Publication Data
US 2004/0102711 A1 May 27, 2004

Related U.S. Application Data

(63) Continuation-in-part of application No. 10/046,767, filed on Jan. 17, 2002, now abandoned.

(51) Int. Cl.
*A61M 16/00* (2006.01)

(52) U.S. Cl. ............ 128/200.26; 128/207.14

(58) Field of Classification Search ......... 128/200.26, 128/848, 859, 860, 861, 200.29, 201.11, 201.26, 128/205.19, 205.23, 206.29, 207.11, 207.14, 128/207.15, 207.16; 606/191, 196; 604/77, 604/79
See application file for complete search history.

(56) References Cited

U.S. PATENT DOCUMENTS

| | | | |
|---|---|---|---|
| 1,498,810 A | 6/1924 | Poe | |
| 2,127,215 A | 8/1938 | Gwathmey | 128/208 |
| 3,306,298 A | 2/1967 | Raimo | 128/351 |
| 3,419,004 A | 12/1968 | Berman | 128/208 |
| 3,756,244 A | 9/1973 | Kinnear et al. | 128/351 |
| 3,774,616 A | 11/1973 | White et al. | 128/351 |
| 3,926,196 A | 12/1975 | Bornhorst et al. | 128/351 |
| 4,067,331 A | 1/1978 | Berman | 128/208 |
| 4,198,970 A | 4/1980 | Luomanen | 128/207.15 |
| 4,300,550 A | 11/1981 | Gandi et al. | 128/207.18 |
| 4,425,911 A | 1/1984 | Luomanen et al. | 128/200.26 |
| 4,651,746 A | 3/1987 | Wall | 128/670 |
| 4,882,867 A * | 11/1989 | Linden | 40/625 |
| 4,948,547 A | 8/1990 | Hendry | 264/500 |
| 5,028,377 A | 7/1991 | Hendry | 264/572 |
| 5,039,463 A | 8/1991 | Loren | 264/40.3 |
| 5,080,570 A | 1/1992 | Baxi et al. | 425/130 |
| 5,204,050 A | 4/1993 | Loren | 264/504 |
| 5,205,281 A | 4/1993 | Buchanan | 128/207.14 |
| 5,208,046 A | 5/1993 | Shah et al. | 425/130 |
| 5,284,429 A | 2/1994 | Schneider et al. | 425/130 |
| 5,295,800 A | 3/1994 | Nelson et al. | 425/130 |
| 5,318,017 A | 6/1994 | Ellison | 128/200.24 |
| 5,555,890 A * | 9/1996 | Schaller | 600/532 |
| 5,803,731 A | 9/1998 | Nordström | 433/96 |

(Continued)

FOREIGN PATENT DOCUMENTS

CA 574736 4/1959

(Continued)

*Primary Examiner*—Teena Mitchell
(74) *Attorney, Agent, or Firm*—Thomas, Kayden, Horstemeyer & Risley LLP

(57) ABSTRACT

An oro-pharyngeal airway includes external air passages (28) formed between it and the facing surfaces of the patient's throat for continuous breathing by the patient. The open-ended passage (26) of conduit (24) transmits exhaled breath of the patient directly from the distal end of the airway at the larynx into the plenum (50) at the proximal end of the airway, and the breath is extracted radially from the plenum though the conduit section (34) and is analyzed by monitor (40). Alternatively, oxygen can be provided from source (42) through the converging conduit section (32) of the elongated body, and mucus, etc. can be aspirated from the larynx area of the throat by suction pump (44). These functions can take place without the need for additional intubation of the patient.

11 Claims, 2 Drawing Sheets

U.S. PATENT DOCUMENTS

| | | | |
|---|---|---|---|
| 6,244,865 B1 | 6/2001 | Nelson et al. | 433/140 |
| 6,256,524 B1 | 7/2001 | Walker et al. | 600/340 |
| 6,386,199 B1 | 5/2002 | Alfery | 128/207.15 |
| 6,481,436 B1 | 11/2002 | Neame | 128/200.26 |
| 2003/0131853 A1 | 7/2003 | Wall, Jr. et al. | 128/107.14 |

FOREIGN PATENT DOCUMENTS

| | | |
|---|---|---|
| CA | 814744 | 6/1969 |
| CA | 1005721 | 2/1977 |
| CA | 1161720 | 2/1984 |

* cited by examiner

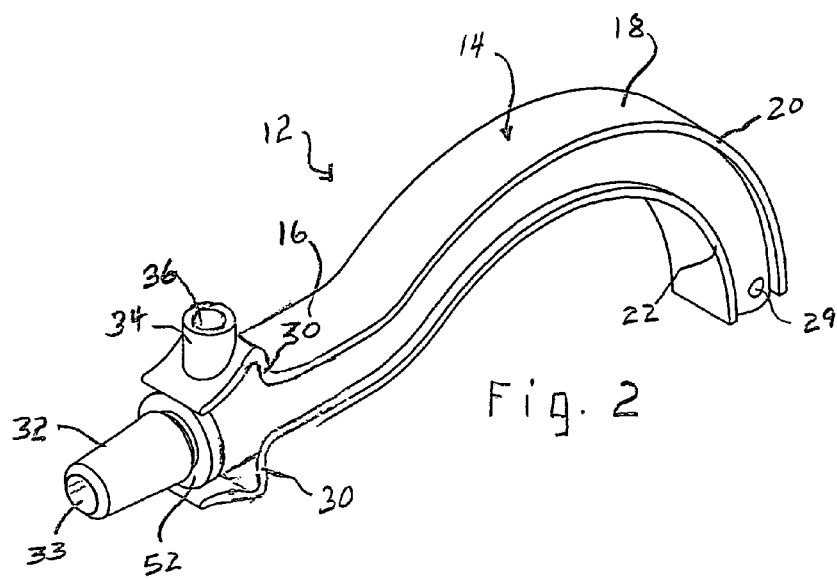
Fig. 2
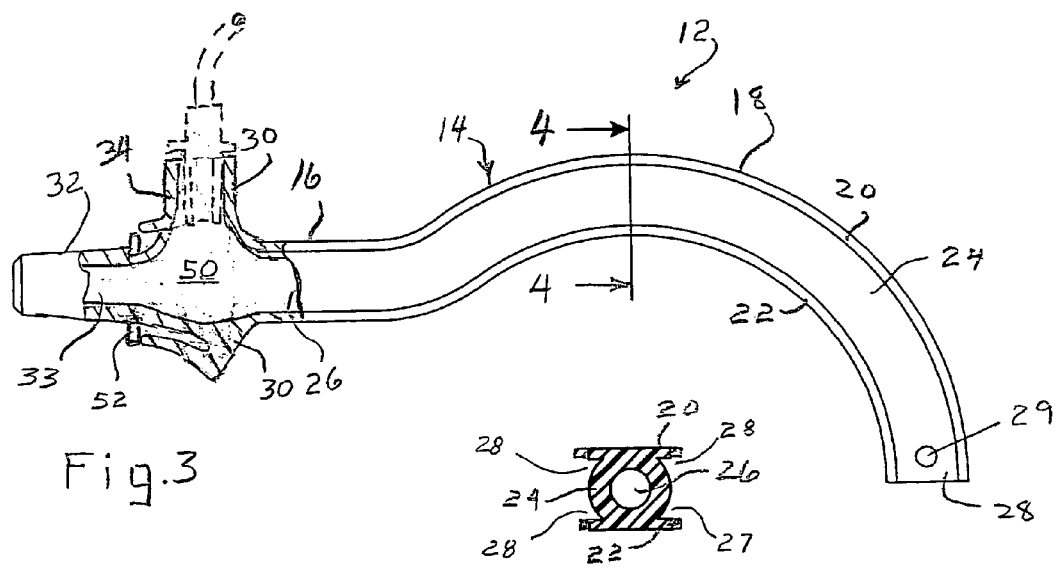
Fig. 3
Fig. 4

ORO-PHARYNGEAL AIRWAY WITH BREATH MONITOR

CROSS REFERENCE TO RELATED APPLICATION

This application is a continuation-in-part of U.S. patent application Ser. No. 10/046,767 filed Jan. 17, 2002, now abandoned.

FIELD OF THE INVENTION

This invention relates generally to an Oro-Pharyngeal Airway, and more specifically to an airway that can be combined with a carbon dioxide monitor, that is used for a sedated or unconscious patient, such as when a patient is under or recovering from anesthesia, for detecting the carbon dioxide in the breath exhaled from the patient.

BACKGROUND OF THE INVENTION

During surgical procedures, particularly when the patient is under or recovering from general anesthesia, it is highly desirable to monitor the carbon dioxide of the breath exhaled by the patient. The amount of carbon dioxide in the exhaled breath, particularly at the end of the respiratory cycle, known as $ETCO_2$, indicates the health of the patient, and can be used to forecast changing conditions of the patient.

The American Society of Anesthesiologists implemented a new standard mandating the use of carbon dioxide ($CO_2$) monitoring during all general anesthesia, whether in or out of the operating room, for both intubated and non-intubated patients. This new standard of care necessitates recognition, support, and compliance by key personnel involved in the management and delivery of anesthesia and procedural sedation. As the use of procedural sedation expands beyond the operating room, implementation of the standard becomes relevant to a broad spectrum of settings including hospitals and ambulatory care facilities as well as office-based practices for medical, surgical, dental, and oral surgery offices. Capnography, the monitoring of carbon dioxide in the patient's expelled breath, significantly reduces patient's safety risks by giving the earliest detection of hypoventilation.

Some authorities indicate that capnography should now be considered an essential component of patient monitoring in all situations in which drugs are given that impact levels of consciousness, responsiveness, and airway protective reflexes.

Qualitative clinical signs such as chest excursion, observation of the reservoir breathing bag, and auscultation of breath sounds are useful. Continual monitoring for the presence of expired carbon dioxide is to be performed unless invalidated by the nature of the patient procedure or equipment.

In addition, monitoring of other aspects of the patient's breath can also be beneficial, such as the detection of certain drugs, alcohol, DNA, antibodies (including tumor), blood sugar, billirubin, acetone, and other elements in organic and inorganic compounds that might be present in the body.

Preferably, the sample of the patient's breath should be collected next to the opening of the larynx at the end of the respiratory cycle so that the tested sample will have minimal dilution from the ambient air, therefore be a truer sample for analysis.

Respiration devices and alarm systems for such devices are known in the art. Alarms are provided for alerting an operator when a patient is not breathing or the patient's breathing is failing outside of a normal breathing pattern. Such respiratory devices that are provided with alarms are disclosed in U.S. Pat. Nos. 3,798,629; 3,802,417; 3,961,627; 4,287,886; 4,366,821; 4,368,740; 4,413,632; 4,417,589; and in my prior U.S. Pat. No. 4,651,746. However, it is desirable to monitor the breath exhaled by the patient at the larynx to provide the evaluation of breath undiluted by ambient air or other conditions of the throat and mouth.

Another desired situation for monitoring exhaled breath is that the intubation device that reaches the larynx should have the ability to perform several functions, such as insufflation of medication directly to the larynx area of the throat, aspiration of mucus from the throat, monitoring of the breath expelled from the larynx area of the throat, and maintaining a continuously open airway for continuous breathing by the patient, all without removal of the oro-pharyngeal airway from the throat. This is particularly important for infants and children of small size because the small change in condition can be traumatic for the smaller body. Early detection of the change in breath condition of the smaller patient might be critical.

It is to these problems and objectives that this invention is directed.

SUMMARY OF THE INVENTION

Briefly described, the present invention concerns a method and apparatus for monitoring the carbon dioxide of a patient's breath, particularly the portion of the breath exhaled at the end of the respiratory cycle from the vicinity of the larynx of the patient's throat during the time when the patient is unconscious, as when the patient is recovering from general anesthesia or when the patient is otherwise incapable of communicating with the surgeon or other medical staff. The monitoring of the patient can be accomplished with a multi-function airway placed in the patient's throat that permits other procedures to be performed without removing the airway.

In the preferred embodiment, an oro-pharyngeal airway is provided for insertion into the patient's throat. The airway includes an elongated body that is curved to fit the shape of the throat and having a proximal end for placement at the mouth of the patient and a distal end that extends through the throat to the vicinity of the larynx. The elongated body is provided in different sizes and is shaped to be compatible with the size and shape of the patient's throat, by providing airways of different lengths and breadths. The proximal end of the body of the airway is sized and shaped for engagement by the person's mouth, having a radially extending protrusion configured to block the movement of the proximal end into the patient's mouth, thereby stabilizing the proximal end at the mouth of the patient, accessible to the physician.

The elongated body of the airway defines an open-ended passage extending through the length of the body and being open at the proximal and distal ends of the elongated body. A front conduit segment or nipple extends beyond the radially extending member, with its opening that is approximately coextensive with the open-ended passage. A second conduit segment is positioned between the nipple and the radially extending protrusion so that it will be located outside the patient's mouth. The second conduit segment extends approximately radially from the elongated body with its passage formed in a T-shaped intersection with the passages of the nipple and the elongated body. The T-shaped intersection of the passages is of larger breadth and volume than the open ended passage of the elongated body of the airway. The T-shaped intersection forms a plenum outside of the patient's mouth for the accumulation of the exhaled breath of the patient. This larger plenum chamber can accumulate the breath at the end of the respiratory cycle at the proximal end of the airway and progressively feed the end tidal to the monitor at the rate induced by the monitor for a more even measurement of the carbon dioxide or other gas to be detected and measured. The placement of the plenum at the nipple end of the airway allows the airway to include the plenum without increasing the external breadth of the airway that extends into the throat, thereby keeping the external breadth of the elongated body of the airway as small as practical.

External protrusions extend from the elongated body of the airway and are shaped to engage the facing surfaces of the throat of the patient and form breathing passages that straddle the elongated body and extend along and externally of the elongated body. This provides the patient with a pair of air passages formed along the throat regardless of the manipulation of the open-ended passage extending through the length of the elongated body of the airway.

When in use, the nipple typically will be connected to a suction device that can intermittently aspirate the throat of the patient through the open ended passage, clearing mucus from the throat and maintaining the air passages that straddle the airway open for breathing. Also, a supply of oxygen can be connected to the same nipple for the purpose of supplying oxygen to the lungs of the patient. Other devices such as an insufflation device can be used to move airborne medication through the open-ended passage to the larynx and lungs. In the meantime, the radially extending conduit that intersects the air passage of the airway can remain closed by the use of a plug or by the attendant's finger covering the opening thereof for controlling the effectiveness of the aspiration or insufflation of the throat, or can be connected to a monitoring device that monitors the content of the exhaled breath of the patient, particularly the breath at the end of the respiratory cycle. The monitor can be a carbon dioxide monitor.

The monitoring device usually will include an open-ended flexible tube having a first end connected to the radially extending conduit of the airway and its other end connected to the monitoring device. This provides an uncontaminated source of the patient's breath taken at the larynx without dilution or contamination from other sources along the throat and mouth and ambient air about the mouth of the patient.

A monitor suitable for this use is a capnographic monitor. When the monitor detects an increase or decrease in the carbon dioxide of the patient's breath, this becomes a forecast as to the health of the patient. A noticeable increase in the detection of carbon dioxide indicates, for example, hypoventilation by the patient, whereas a noticeable decrease in the detection of carbon dioxide indicates, for example, recovery from hypoventilation by the patient. This information can be used to decide what drugs are to be used to stabilize the patient.

In general, the invention includes a method of monitoring the carbon dioxide of a patient's breath while the patient is under general anesthesia. This includes intubating the patient's throat with an airway having an air conduit extending therethrough and extending from the mouth of the patient to the larynx of the patient, while maintaining an air passage between the airway and the facing surfaces of the patient's throat to permit the patient to breathe about the airway. Breath is withdrawn from about the larynx of the patient through the air conduit of the airway to a carbon dioxide monitor, and a carbon dioxide monitor is used for monitoring the carbon dioxide content of the patient's breath as it is withdrawn from about the larynx of the patient Another feature of the invention may include the step of injecting a gas through the air conduit extending through the airway to the larynx, and wherein the step of withdrawing breath from about the larynx of the patient comprises intermittently withdrawing the breath. The step of injecting gas to the larynx may include intermittently injecting gas, and wherein the steps of withdrawing breath and injecting gas are performed alternately.

The step of injecting gas through the air conduit may include moving the gas through the first nipple that is coextensive with the air conduit, and the step of withdrawing breath from about the larynx comprises moving the breath through the second nipple that intersects the air conduit.

The step of withdrawing breath from the patient may include attaching one end of a flexible open-ended tube to the airway in communication with the air conduit and extending the other end of the open-ended tube to a carbon dioxide monitor.

The step of withdrawing breath from the larynx comprises moving the breath from the larynx to a plenum chamber in the airway and then moving the breath from the plenum chamber to the monitoring device.

Also, the airway is characterized by having been formed of polymer material by simultaneously feeding polymer material and nitrogen gas into the cavity of a mold so that the nitrogen gas pushes the polymer material against the cavity walls of the mold so that the polymer material forms the airway.

BRIEF DESCRIPTION OF THE DRAWINGS

FIG. 2 is a perspective illustration of the airway.

FIG. 3 is a side elevational view of the airway, partially in cross section to show the plenum at the proximal end of the airway.

FIG. 4 is a cross-sectional view of the elongated body portion of the airway, taken along line 4 of FIG. 3.

DETAILED DESCRIPTION

Figure 1:
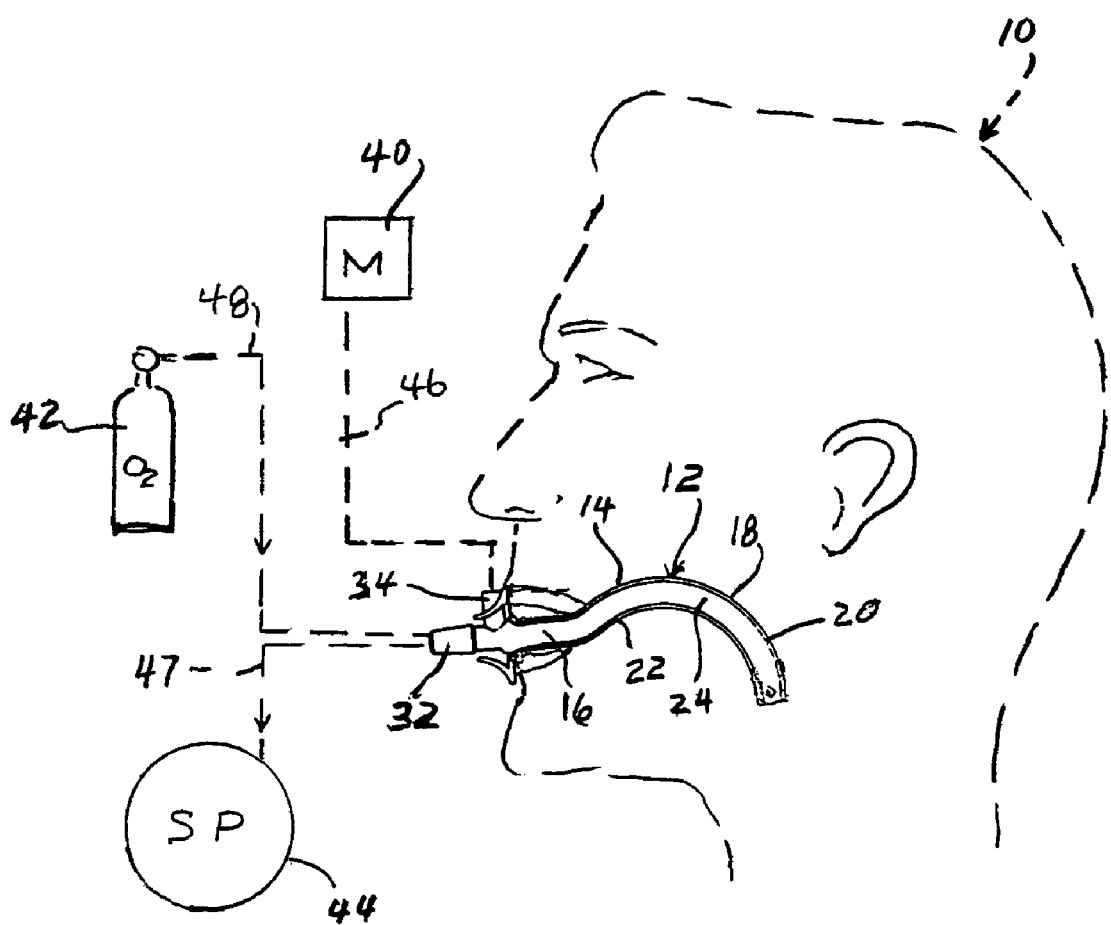
FIG. 1 is a side view of the airway, showing the airway positioned in the throat of a patient, with the patient shown in dash lines, and with the monitor, oxygen supply and pump shown schematically connected to the airway.

Referring now in more detail to the drawings in which like numerals indicate like parts throughout the several views, FIG. 1 shows a patient 10 that is intubated with the airway 12, with the airway extending to the larynx of the patient. The airway, shown better in FIGS. 2-4, includes an elongated body 14 formed of a suitable substantially rigid material, such as a relatively light-weight thermoplastic that can be gas assisted injection molded into the detailed shape. The gas assisted injection method is in any conventionally known method. This is important to the invention to provide the smooth and precisely formed small exterior of the airway that can pass along the throat of the patient, particularly the small patient, while providing a thin wall for forming ample breadth of passage through the interior. While the shapes and sizes of the exterior surfaces of the device are important since they contact the patient, the shapes and sizes of the internal surfaces of the elongated body 14 are not necessarily critical to the operation and function of the invention. Therefore, gas assisted injection molding is a suitable and most desirable form of manufacture of the device.

The elongated body 14 includes a proximal straight section 16 and a distal arcuate section 18. A pair of opposed, spaced, longitudinally extending parallel ribbon-like flange elements 20 and 22 are formed on opposite surfaces of conduit 24. An internal, open-ended passage 26 (FIG. 4) extends throughout the length of the elongated body 14. The passage 26 terminates in open end 28, with side ports 29 opening to the side of the conduit 24 at its distal end.

The flanges 20 and 22 protrude laterally of the conduit 24, and are sized and shaped to engage the facing surfaces of the throat of the patient, so that the throat surfaces and the flanges, together with the external surface of the conduit 24, form external air passages 27 about the elongated body, so that the patient has open air passages to the outside along the entire length of the elongated body 14.

The proximal end 16 of the elongated body 14 terminates in radial protrusions 30 that are formed by a pair of radially extending flanges. This forms a rest for the airway to rest against the lips of the patient when the patient is intubated with the airway, as shown in FIG. 1.

A nipple or converging conduit section 32 is mounted to the proximal straight section 16 of the elongated body 14, with its passage 33 coextensive with the passage 26 of the elongated body 14. The nipple 32 is formed in a diverging shape so as to be compatible with a friction fit with interior surface of the end of a flexible conduit (not shown) wedged onto the exterior surface of the nipple, when connecting other devices to the airway. In the alternative, the internal passage of the conduit section 32 can be formed in a converging configuration for the wedging of a smaller end portion of a flexible conduit into the passage. Moreover, other connector configurations can be utilized for screwing, clamping, or other conventional means of connecting the flexible conduit to the conduit section 32 of the airway.

A T-shaped connection is formed by radially extending conduit section 34, and its open-ended passage 36 communicates with the passage 26 of the elongated body 14 and passage 33 of nipple 32. Like the converging conduit section 32, the radially extending conduit section 34 can be of various shapes to expedite the connection of the end portion of an open-ended flexible tube.

It will be noted that the radially extending conduit section 34 is positioned on the distal side of the radial protrusion 30, so that the mouth of the patient will not interfere with access to the conduit section 34.

As illustrated in FIG. 1, a monitor, such as a carbon dioxide monitor 40, is connectable to the radially extending conduit section 34 of the airway 12, while other devices, such as an oxygen supply 42 and/or a spray pump 44, are connectable individually or together to the converging conduit section 32 of the airway. The dash lines 46 extending from monitor 40 represent flexible open-ended plastic tubing of conventional design. Similar flexible tubing 47, 48 connects the suction pump 44 and oxygen supply 42 to the nipple 32.

FIG. 3 illustrates the T-shaped intersection of the passage 36 of the radial conduit section 34 with the passages 26 and 33 of the nipple 32, and elongated body 14. The dimensions of the T-shaped intersection are of greater breadth than the passages 26 and 33, forming a plenum generally designated at 50 that is at least twice as large, preferably four times as large as the breadths of the nipple passage 33 and the open ended passage 26. The plenum is located at the proximal end of the airway, at a position beyond the radial protrusion 30 and beyond where the mouth of the patient is to be placed. This avoids the placement of the plenum in the elongated body of the airway where the size of the airway is to be kept as small as practical. The plenum 50 functions to accumulate a large volume of the exhaled breath from the larynx of the patient, preferably at the end of the respiratory cycle of the patient, forming a larger supply of exhaled breath with high content of carbon dioxide that can be delivered to the monitor at the rate induced by the monitor.

As stated above, the airway can be manufactured in different sizes for use with patients of different sizes. A different color is applied to each different size airway to designate the size of the airway. The color in the disclosed embodiment is carried by a collar 52 that surrounds the base of the nipple, but the color identifier can be applied in different ways, such as the material of the airway being formed in colors that correspond to the size of the airway.

OPERATION

The apparatus can be used in several ways, such as utilizing the suction pump 44 to withdraw mucus from the throat of the patient deep within the throat adjacent the larynx, using the oxygen supply 42 to supply the patient with oxygen, and utilizing the monitor 40 to analyze the breath of the patient, particularly the carbon dioxide content of the breath for the purpose of predicting the physical condition of the patient. Conventional valves (not shown) are used to open and close communication between the airway and the oxygen supply, the suction pump and the monitor so these devices can be use one at a time.

It will be noted that the distal end portion 18 of the elongated body 14 is placed deep within the throat, adjacent the larynx, so that its passage 26 opens through the open end 28 and the lateral air opening 29. This allows the suction pump 44 to withdraw the mucus from adjacent the larynx, and also allows the monitor 40 to monitor the condition of the breath at the larynx, before the breath passes through the outer portion of the throat, through the mouth into the atmosphere, thereby avoiding contamination of the breath with additional outside air or other conditions of the throat and mouth. Thus, a more pure sample of the content of the patient's exhaled breath can be obtained with this invention. In addition, the monitoring of the patient's exhaled breath can be continued without requiring further intubation of the patient, without interrupting the other intermittent functions of the airway, and without significant discomfort or injury to the patient.

In operation of the oro-pharyngeal airway 12, the device is inserted into the patient's mouth until the curved distal section 18 extends through the back of the patient's throat, adjacent the pharynx. In the meantime, the radial protrusion 30, in the form of oppositely extending flanges, comes to rest against the exterior of the patient's mouth, avoiding inadvertent movement of the proximal end further into the mouth of the patient. The flanges 20 and 22 engage the facing surfaces of the patient's throat, forming the air passages 28. Since the flanges 20 and 22 extend along the entire length of the airway, the air passages formed on opposite sides of the elongated body will not be interrupted by any of the functions that are carried on internally of the airway. The patient is then able to breathe through the channels 28 that extend along the exterior of the conduit 24 of the elongated body 14.

In addition to the ability of the patient to breathe exteriorly of the elongated body 14, the patient can also breathe through the internal passage 26 of the airway, as long as the passage is open and not being used for other purposes.

When it is necessary to perform a throat evacuation to remove fluid, mucus, blood, etc. from the throat, a flexible tubular conduit represented by the dash lines 47 of FIG. 1 is frictionally engaged over the converging conduit section 32 of the airway. The suction pump apparatus 44 is connected to the distal end of the flexible tube and is operated to create a mild suction within the passage 26 of the airway 12, withdrawing such fluids from the patient's throat. This can be performed without removing the suction airway 12 from the patient's mouth.

Alternatively, insuflation of the patient's lungs can be accomplished by connecting the tube to a insuflation device, such as an oxygen supply apparatus 42 in order to inject a stream of oxygen through the passage 26 of the airway, through the distal end 28, down the patient's throat, to the patient's lungs.

During either the suction or oxygen supply operations, the patient is still able to breathe through the side air channels or passages 28 formed between the airway and the facing surfaces of the throat.

The radially extending conduit section 34 can be used as a valve by the attending physician, either covered or opened, to control the strength of the suction of the suction pump 44, by applying the attendant's fingertip to the passage 36 of the radially extending conduit section 34.

More importantly, the carbon dioxide content of the patient's exhaled breath can be monitored by the application of a flexible tube to the radially extending conduit section 34, and extending the other end of the tube to a monitor 40. This causes the exhaled breath of the patient to be moved directly to the monitor 40 without contaminating the sample of breath with ambient air adjacent the patient's mouth or other contaminants derived from the throat and/or mouth of the patient.

Although preferred embodiments of the invention have been disclosed in detail herein, it will be obvious to those skilled in the art that variations and modifications of the disclosed embodiments can be made without departing from the spirit and scope of the invention as set forth in the following claims.

What is claimed is:

1. A method of monitoring the carbon dioxide of a patient's breath while the patient is under general anesthesia, comprising:
    intubating the patient's throat with an airway having an open ended air conduit extending therethrough and extending through a plenum of larger breadth than the open ended air conduit formed on the airway and to the larynx of the patient,
    maintaining an air passage between the airway and the facing surfaces of the patient's throat to permit the patient to breathe about the airway,
    inducing the patient to exhale through the open ended conduit of the airway and the plenum,
    withdrawing breath from about the larynx of the patient through the air conduit of the airway and through the plenum and to a carbon dioxide monitor without interrupting the air passage, and
    monitoring the carbon dioxide content of the patent's breath withdrawn from about the larynx with the carbon dioxide monitor.

2. The method of claim 1, and further including the step of injecting a gas through the air conduit extending through the airway to the larynx,
    and wherein the step of withdrawing breath from about the larynx of the patient comprises intermittently withdrawing breath,
    and wherein the step of injecting gas to the larynx comprises intermittently injecting gas,
    and wherein the steps of withdrawing breath and injecting gas are performed alternately.

3. The method of claim 2, wherein the step of injecting gas through the air conduit
    comprises moving the gas through a first nipple that is co-extensive with the air conduit, and
    the step of withdrawing breath from about the larynx comprises moving the breath through a second nipple that intersects the air conduit.

4. The method of claim 1, wherein the step of withdrawing breath from the patient comprises attaching one end of a flexible open ended tube to the plenum and extending the other end of the open ended tube to the carbon dioxide monitor.

5. Apparatus for monitoring the carbon dioxide of a patient's breath when under anesthesia, comprising:
    an oro-pharyngeal airway for insertion into a person's throat comprising:
    an elongate body having a proximal end and a distal end,
    said proximal end of said body sized and shaped for engagement by a person's mouth and having a radially extending member configured to block the movement of said proximal end into the patient's mouth,
    said body being of a predetermined length so that when said proximal end is at the patient's mouth said distal end is positioned at the person's larynx,
    said elongate body defining an open ended passage extending through the length of said body and being open at the proximal and distal ends of said body,
    a nipple extending beyond said radially extending flange, said nipple having an opening that is co-extensive with said open ended passage,
    a radially extending conduit having a passage therethrough in communication with said open ended passage of said elongate body and said opening of said nipple, for the passage therethrough of breath exhaled from the area of the patient's larynx,
    a plenum for accumulating the exhaled breath of the patient positioned at said radially extending conduit for placement outside the patient's mouth,
    said plenum being in communication with both said open ended passage of said elongate body and said passage of said radially extending conduit,
    said plenum being of larger breadth than either of said passage of said radially extending conduit and said open ended passage of said elongated body,
    protrusions extending from said elongate body shaped to engage the facing surfaces of the throat of the patient and form a breathing passageway extending along and externally of said elongate body, and
    a carbon dioxide monitor in communication with the passage of said radially extending conduit for detecting the carbon dioxide received through the conduit of said body from the distal end of the body at the larynx of the patient.

6. The apparatus of claim 5, wherein said airway is constructed of a thermoplastic polymer and said airway is characterized by having been formed in a gas assisted injection mold.

7. The apparatus of claim 6, wherein a color is applied to said airway that is in contrasting color with respect to said body to denote a preselected identifying external size of said body.

8. The apparatus of claim 6, wherein a color is applied to said airway that corresponds to the external size of said body.

9. Apparatus for monitoring carbon dioxide of a patient's breath, comprising:

an oro-pharyngeal airway for insertion in the throat of a patient, said airway having a proximal end for placement at the patient's mouth and a distal end for placement through the patient's throat adjacent the larynx of the patient, said airway defining an open ended, approximately cylindrical passage therethrough, ribs extending externally along the length of the airway for engagement with the facing surface of the throat of the patient for forming an external passage about the airway so that the patient can breath about the airway, a nipple at said proximal end of said airway extending co-extensively from said passage for connection with a suction device or an insufflation device, a protrusion at said proximal end of said conduit between said nipple and said conduit for engagement by the lips of the patient to prevent the proximal end of the airway from entering the mouth of the patient, a T-connection formed between said protrusion and said nipple and an orifice extending through said T-connection to said passage of said airway for controlling the movement of breath exhaled from the patient through said passage, said orifice at said T-connection being of at least twice greater in cross sectional area than said central passage of said airway and forming a plenum for accumulating the exhaled breath of the patient, and a carbon dioxide monitor in communication with said T-connection for detecting the carbon dioxide in the patient's breath received from about the larynx without having passed through the mouth of the patient.

10. The apparatus of claim 9, wherein said airway is characterized by having been formed of polymer material by simultaneously feeding polymer material and nitrogen gas into the cavity of a mold so that the nitrogen gas pushes the polymer material against the cavity walls of the mold so that the polymer material forms the airway.

11. Apparatus for monitoring carbon dioxide of a patient's breath, comprising:

an oro-pharyngeal airway for insertion in the throat of a patient, said airway having an elongated body with a proximal end for placement at the patient's mouth and a distal end for placement through the patient's throat adjacent the larynx of the patient, said elongated body of said airway defining an open ended passage therethrough, ribs extending externally along the length of said elongated body of the airway for engagement with the facing surface of the throat of the patient for forming an external passage about the airway so that the patient can breath about the airway, a nipple at said proximal end of said elongated body of said airway and defining a passage extending co-extensively from said open ended passage of said elongated body, a T-connection formed at said nipple with a passage of the T-connection intersecting the passage of said nipple and the open ended passage of said elongated body, said T-connection forming a plenum of a breadth at least twice as large as the breadth of said airway for receiving the exhaled breath of the patient, and a breath monitor in communication with said T-connection for receiving the patient's breath from said plenum and detecting the content of the patient's breath received from about the larynx without having the breath passed in contact with the mouth of the patient.

* * * * *